(12) United States Patent
Khatri

(10) Patent No.: US 8,119,831 B2
(45) Date of Patent: Feb. 21, 2012

(54) MOISTURE ACTIVATED LATENT CURING ADHESIVE OR SEALANT

(75) Inventor: Chetan Anirudh Khatri, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 12/570,350

(22) Filed: Sep. 30, 2009

(65) Prior Publication Data
US 2010/0087672 A1   Apr. 8, 2010

Related U.S. Application Data

(62) Division of application No. 11/501,541, filed on Aug. 9, 2006.

(51) Int. Cl.
*C07C 69/34* (2006.01)
*C07C 69/52* (2006.01)
*C07C 263/00* (2006.01)
*C07C 265/00* (2006.01)

(52) U.S. Cl. .................... 560/190; 560/330
(58) Field of Classification Search .............. 523/115; 560/190, 330
See application file for complete search history.

(56) References Cited

U.S. PATENT DOCUMENTS

| | | | |
|---|---|---|---|
| 3,267,078 A | 8/1966 | Damusis | |
| 3,793,417 A | 2/1974 | Erikson et al. | |
| 4,430,489 A | 2/1984 | MacMillan et al. | |
| 4,570,270 A | 2/1986 | Oechsle, III | |
| 4,804,691 A | 2/1989 | English et al. | |
| 4,829,099 A | 5/1989 | Fuller et al. | |
| 5,198,524 A | 3/1993 | Bush et al. | |
| 5,874,500 A | 2/1999 | Rhee et al. | |
| 5,990,194 A | 11/1999 | Dunn et al. | |
| 6,166,130 A | 12/2000 | Rhee et al. | |
| 6,328,229 B1 | 12/2001 | Duronio et al. | |
| 6,352,710 B2 | 3/2002 | Sawhney et al. | |
| 6,525,159 B1* | 2/2003 | Okuhira et al. | 528/26 |
| 6,534,591 B2 | 3/2003 | Rhee et al. | |
| 6,864,350 B2 | 3/2005 | Harris | |
| 6,899,889 B1 | 5/2005 | Hnojewyj et al. | |
| 7,129,300 B2 | 10/2006 | Roby | |
| 7,241,846 B2 | 7/2007 | Roby | |
| 7,259,190 B2 | 8/2007 | Lykke | |
| 7,947,758 B2 | 5/2011 | Khatri et al. | |
| 2002/0165337 A1 | 11/2002 | Wallace et al. | |
| 2003/0012734 A1* | 1/2003 | Pathak et al. | 424/9.6 |
| 2004/0023842 A1 | 2/2004 | Pathak et al. | |

(Continued)

FOREIGN PATENT DOCUMENTS
EP    1165716    10/2004

(Continued)

OTHER PUBLICATIONS

Polymeric Biomaterials, 2nd Ed., Marcel Dekker Inc. (2002) pp. 716.

(Continued)

*Primary Examiner* — Mark Eashoo
*Assistant Examiner* — David Karst
(74) *Attorney, Agent, or Firm* — David R. Crichton

(57) ABSTRACT

The invention relates to a novel poly(ethylene oxide)imine; a novel amine reactive moiety; a novel moisture activated latent curing adhesive or sealant mixture comprising (1) a ketimine or aldimine, and (2) an amine reactive moiety; and a novel moisture activated latent curing adhesive or sealant comprising the reaction product of (1) and (2).

1 Claim, 3 Drawing Sheets

U.S. PATENT DOCUMENTS

| | | | |
|---|---|---|---|
| 2004/0219214 A1* | 11/2004 | Gravett et al. | 424/484 |
| 2005/0053576 A1* | 3/2005 | Tanaka et al. | 424/78.27 |
| 2007/0031498 A1 | 2/2007 | Zong et al. | |
| 2008/0039547 A1 | 2/2008 | Khatri et al. | |
| 2008/0039548 A1 | 2/2008 | Zavatsky et al. | |

FOREIGN PATENT DOCUMENTS

| | | |
|---|---|---|
| JP | 2000-104037 | 4/2000 |
| WO | WO 89/00589 | 1/1989 |
| WO | WO 94/03155 | 2/1994 |
| WO | WO 2006/076291 | 7/2006 |

OTHER PUBLICATIONS

International Search Report re: PCT/US2007/075418 dated Jan. 16, 2008.

International Search Report re: PCT/US2007/075417 dated Jan. 16, 2008.

International Search Report re: PCT/US2010/053938 dated May 20, 2011.

* cited by examiner

General pathway for gelation

Moisture activated curing of the isocyanate macromer IIIa with ketimine Ia

Synthesis of an amine reactive moiety having an electrophile group and absorbable ester linkages

MOISTURE ACTIVATED LATENT CURING ADHESIVE OR SEALANT

This application is a Divisional claiming priority of U.S. Ser. No. 11/501,541, which was filed on Aug. 9, 2006.

FIELD OF THE INVENTION

The invention relates to a novel polyethylene oxide)imine; a novel amine reactive moiety; a novel moisture activated latent curing adhesive or sealant mixture comprising (1) a ketimine or aldimine, and (2) an amine reactive moiety; and a novel moisture activated latent curing adhesive or sealant comprising the reaction product of (1) and (2).

BACKGROUND OF THE INVENTION

When surgery is performed and wound closure is completed, there is an unmet need for an adhesive or sealant material that will seal the wound site and prevent fluid leakage in, for example, a vessel anastomosis or lung resection. Generally, the key requirements of a tissue adhesive/sealant are:
(1) In use, the adhesive/sealant must mimic the mechanical performance of undamaged tissue;
(2) The adhesive/sealant should provide sufficient tack for "primary" fixation with the opportunity for manipulation and re-alignment prior to setting strongly;
(3) Any exothermic process involved in the curing of the adhesive/sealant should not damage the surrounding tissue;
(4) The adhesive/sealant must not elicit any toxic response by the surrounding healthy tissue and should facilitate the re-growth of new tissue where possible;
(5) The adhesive/sealant should not liberate harmful degradation products;
(6) The adhesive/sealant should degrade, and as it does so, it should be replaced by new tissue with minimal scarring; and
(7) Any biodegradation products should not accumulate in the body but should be eliminated naturally either by excretion or incorporation into the natural biochemical cycle.

["Polymeric Biomaterials", $2^{nd}$ Ed., Marcel Dekker Inc., (2002) pp. 716]

Latent curing adhesives are well known in the field of industrial coatings, adhesives and sealants. For example, a latent curing adhesive may be the reaction product of a two-component mixture, one component being the reactive moiety, such as an epoxy or silicone resin, and the other component being the latent curing agent. More specifically, the latent curing agent may be present in the two component mixture in a non-reactive form, i.e., latent form, during manufacture, storage and non-use, but may then be converted to a reactive curing agent upon application and use. As an example, the latent curing agent may be converted to a reactive curing agent in the presence of moisture that is present in the environment or supplied to the site upon use. It is well known in the art, for example, that a ketimine moiety may be used as a latent curing agent that may be converted to a reactive curing agent, i.e., an amine moiety, in the presence water. After the ketimine moiety has been converted to its amine counterpart, the amine moiety may then react with the second component of the mixture, i.e., a reactive moiety such as an epoxy or silicone resin, to form the desired adhesive and/or sealant. Examples of various ketimines and latent curing adhesives are described in U.S. Pat. No. 6,525,159.

However, the latent curing adhesives described in the prior art are intended for industrial use, and are unsuitable for human use as an internal adhesive or sealant. Therefore, it is desirable to have a moisture-activated latent curing adhesive or sealant mixture that is capable of polymerizing in vivo to form an internal tissue adhesive or sealant. Additionally, it is desirable that such a moisture activated latent curing adhesive or sealant mixture be simple to use and handle, i.e., can be delivered as a single mixture, and is in the form of a flowable mixture that can be delivered to a surgical site, via for example, a syringe.

SUMMARY OF THE INVENTION

The invention relates to a poly(ethylene oxide)imine; an amine reactive moiety; a moisture activated latent curing adhesive or sealant mixture comprising (1) a ketimine or aldimine and (2) an amine reactive moiety; and a moisture activated latent curing adhesive or sealant comprising the reaction product of (1) and (2).

BRIEF DESCRIPTION OF THE FIGURES

FIG. I illustrates a general pathway for the reaction of a ketimine and an amine reactive moiety.

FIG. II illustrates the moisture activated curing of an isocyanate macromer with a ketimine according to Example 2.

Figure 1:
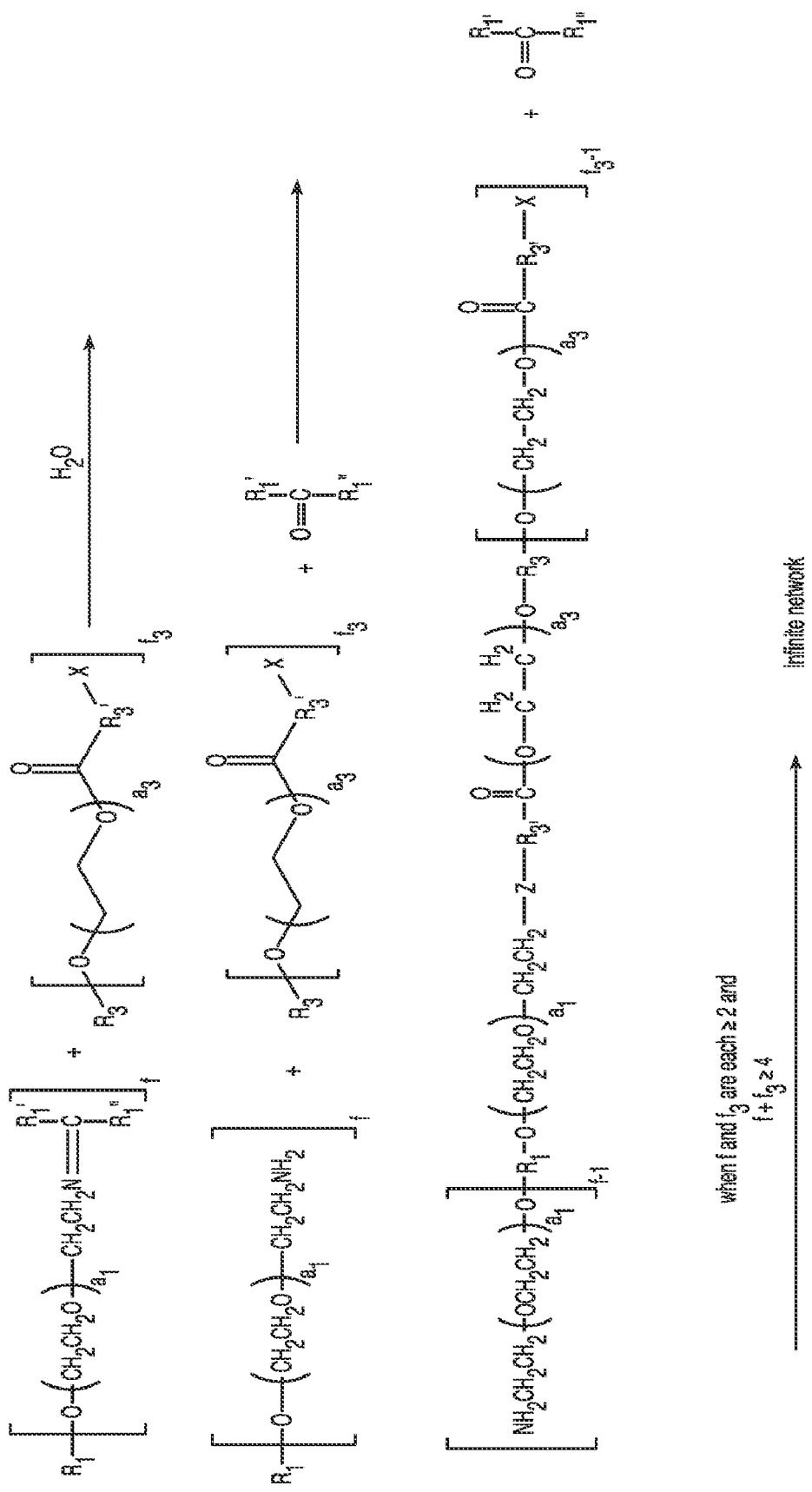
Figure 2:
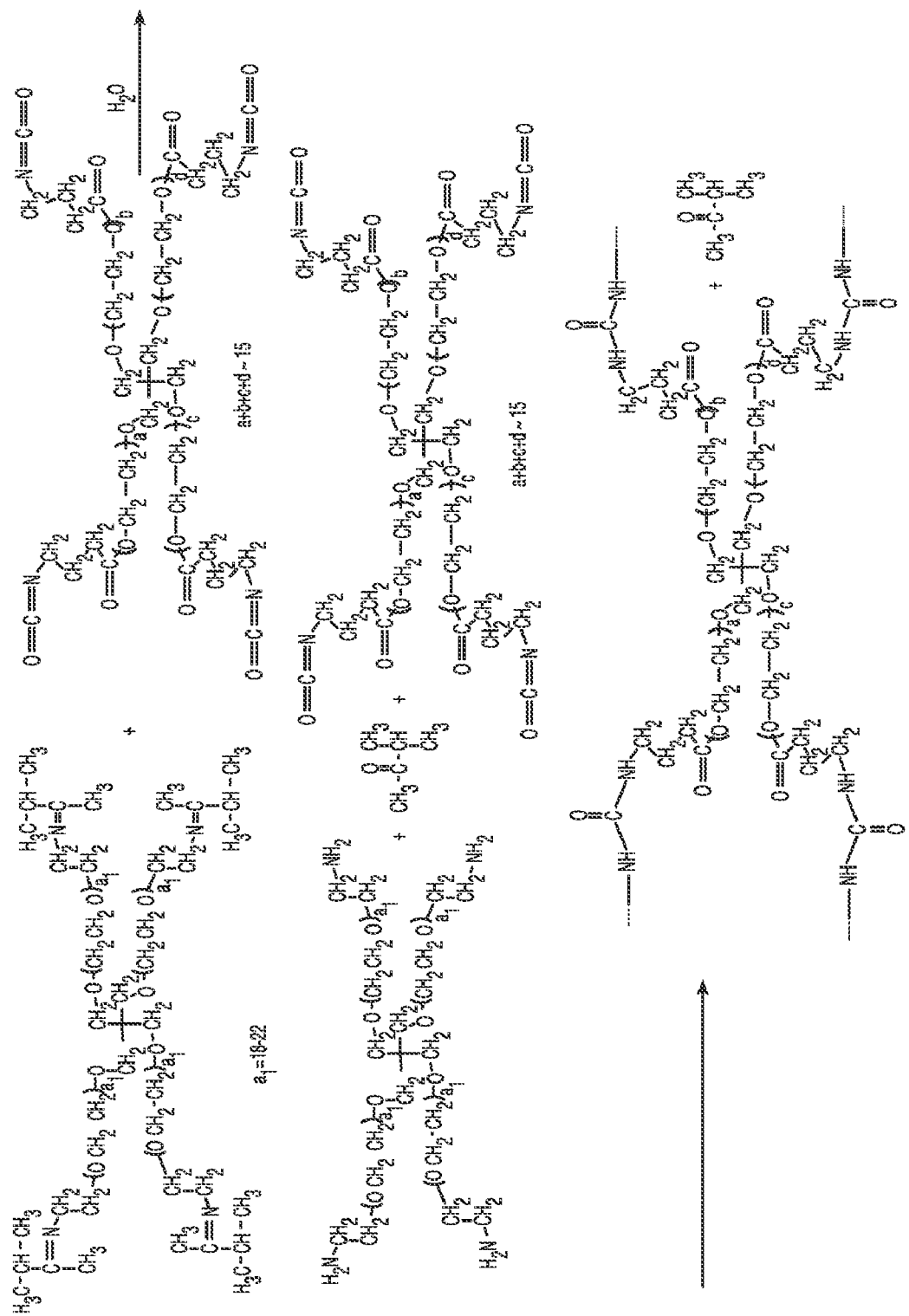
Figure 3:
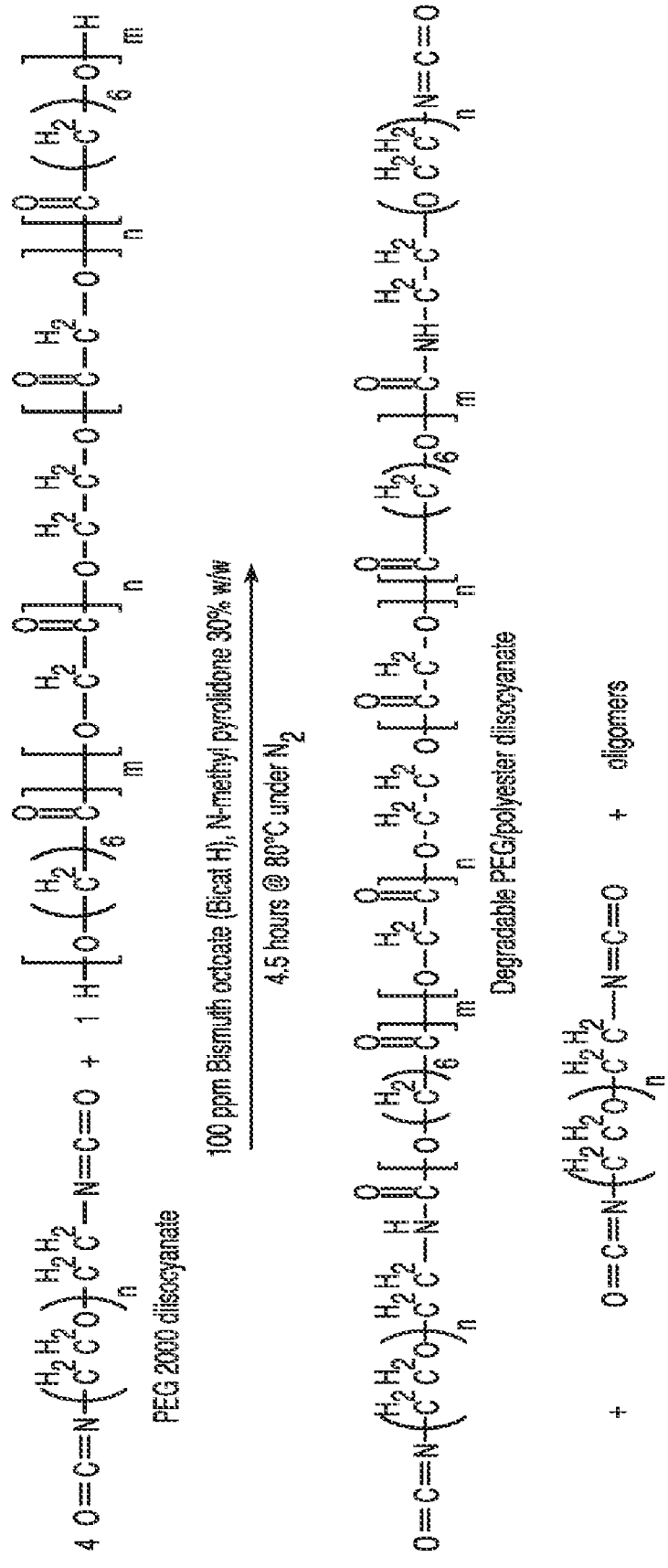

FIG. III illustrates synthesis of an amine reactive moiety having an electrophilic group and absorbable ester linkages.

DETAILED DESCRIPTION OF THE INVENTION

The invention relates to a poly(ethylene oxide)imine; an amine reactive moiety having electrophilic groups; a moisture activated latent curing adhesive or sealant mixture comprising (1) a ketimine or aldimine and (2) an amine reactive moiety; and a moisture activated latent curing adhesive or sealant comprising the reaction product of (1) and (2). The latent curing ability of the adhesive or sealant mixture described herein is imparted by blocking a reactive primary amine with a ketone or aldehyde to form a poly(ethylene oxide)imine. The reaction of the poly(ethylene oxide)imine with the electrophilic groups of an amine reactive moiety is relatively slow, such that these two components may be in intimate contact in a mixture, in the absence of moisture, for extended periods of time, i.e., for up to about 5 hours without premature gelling. By comparison, when the two component mixture is subjected to moisture, the poly(ethylene oxide) imine is "de-blocked" with water to reform the primary amine within about 30 seconds to 3 minutes, which then immediately reacts with the electrophilic groups of the amine reactive moiety.

The latent curing adhesive or sealant mixture according to the present invention has multiple medical applications and may be used in many types of surgery, including, but not limited to, cardiovascular, peripheral-vascular, cardio-thoracic, gynecological, neuro- and general abdominal surgery.

For example, the latent curing adhesive or sealant may be used as an internal surgical adhesive in orthopedic procedures such as anterior cruciate ligament repair, meniscal tear repair (or as a hydrogel for the replacement of the meniscus), posterior capsule reconstruction, rotator cuff repair, and as a bone adhesive. It could also be used as an adhesive for lung volume reduction, patch fixation, subcutaneous tissue repair, and aortic dissection. In particular, it can be used as stomach adhesive for stomach volume reduction, and as adhesive for mesh fixation for hernia repair, drain fixation, valve attachment, attachment for adhesion prevention films, attachment of tissue to tissue (e.g. synthetic or biologic tissue scaffold to tissue, bioengineered tissue to tissue), tissue to device (e.g. mesh, clip, film) and device to device.

Second, the latent curing adhesive or sealant mixture can be used for subcutaneous tissue repair and for seroma prevention in procedures such as mastectomy, breast reconstruction & augmentation, reconstructive or cosmetic abdominoplasty and liposuction, face lift, C-section, hysterectomy in obese patients, orthopedic on thigh region, incisional hernia repair, lipoma excision, traumatic lesions, fistula treatment, graft fixation, and nerve repair.

Third, the latent curing adhesive or sealant can be used as a sealant to attach and seal dural patch products, bile duct, bile leaks in liver bed, bladder leaks, bone graft, burn graft dressing and liquid occlusive dressing. As a sealant, it can be coated on tissue, device, and tissue-device interface and it can be used as dural-cranial sealant, dural-spine sealant, cardio/peripheral vascular sealant, GI sealant (e.g. esophagus, intestine, large organ, pancreas, stomach, and gastric ulcer), lung sealant, soft organ sealant (e.g. liver, spleen, pancreas), bone-wax substitute, tumor sealant, staple/glue combination, sealant/hemostats combination, urethra sealant. It can be used in procedures including, but not limited to, gastric bypass, parenchymatous organs resection, tracheostomy, ulcerative colitis diverticulosis, radical prostatectomy, sinus reconstruction, sternotomy, choledochoduodenostomy, and gallbladder (liver) bed sealing, and cholecystectomy.

Fourth, the latent curing adhesive or sealant can be used as a filler or a periurethral bulking agent in procedures including, but not limited to, dead space removal in reconstructive and cosmetic surgeries, (e.g. plastic/cosmetic/reconstructive, face/facial defect, or void filling), urinary incontinence and other gynecologic procedures, anal fissure/fistula, catheter injection into myocardium for treating congestive heart failure, nuclear augmentation, pancreatic/hepatic cyst/fistula obliteration, and pediatric esophogeal fistula.

Fifth, the latent curing adhesive or sealant can be used as a matrix for tissue engineering (e.g. tissue scaffolds, delivery matrix for cells, delivery matrix for brachytherapy (radiation therapy) agents, delivery matrix for growth factors, injection matrix for in situ-forming empty cell scaffold, injection matrix for scaffold for delivery of stem cells, cell lysate, or other biologics, bioactives, pharmaceuticals, and neutraceuticals, localization matrix for chemotherapy, and localization matrix for contrast agent.

Sixth, the latent curing adhesive or sealant can be used as an adhesion prevention barrier in procedures such as cardiac, open chest, general surgery, obstetrics and gynecological surgeries, orthopedic surgeries, and spine (e.g. artificial disk).

Seventh, the latent curing adhesive or sealant can be used as an occluding material for embolization (e.g. GI Fistula, cerebral/vascular occlusive brain aneurism, tubal occlusion, and varicose vein occlusion).

The Ketimine or Aldimine

The ketimine or aldimine may be an imine macromer such as a poly(ethylene glycol)imine represented by formula I:

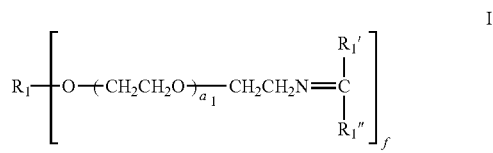

where $3000 \geq a_1 \geq 3$; $6 \geq f \geq 2$; $R_1$ may be a residue of a polyol, i.e., pentaerythritol, glycerols, polyalkylene glycol, and polyols having heteroatoms; $R_1'$ and $R_1''$ are each an alkyl group, i.e., methyl, ethyl, isopropyl or isobutyl group, alkoxy group, i.e., ethoxy or carbalkoxy group, acetoacetate or a hydrogen; and at least one of $R_1'$ or $R_1''$ is an alkyl group having from about 1 to 20 carbon atoms.

Preferably $a_1$ ranges from about 3 to 500; f ranges from 2 to 4; $R_1$ is a residue of pentaerythritol; and $R_1'$ and $R_1''$ are each a methyl and isopropyl group. More preferably $a_1$ ranges from about 18 to 22, and f is 4. The molecular weight of the poly(ethylene oxide)imine may range from about 250 to 10,000, preferably from about 250 to 4000, and more preferably from about 250 to 1000.

An example of such a poly(ethylene oxide)imine with a pentaerythritol core to give a 4-armed-PEG-ketimine of a molecular weight of 4,000, where $a_1$=18-22 is shown in Ia:

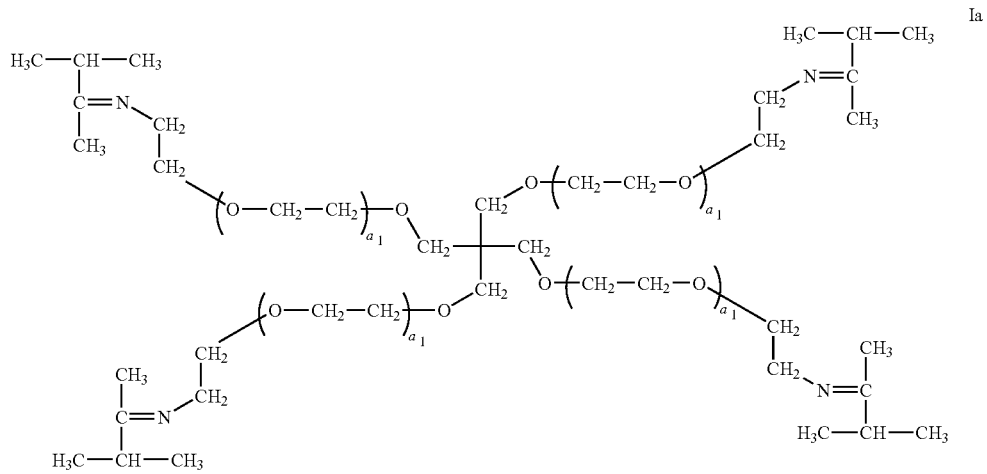

Additional examples of the poly(ethylene oxide)imine include but are not limited to glyceraldimine and isobutylaldimine.

The Amine Reactive Moiety

The imine macromers such as the poly(ethylene oxide) imine represented by Ia may be used as the latent curing agent for an amine reactive moiety having hydrolytically unstable ester linkages and electrophilic groups, including but not limited to isocyanate or N-hydroxy succinimide ester groups, and represented by III, IVa or IVb below:

For example, isocyanate or N-hydroxy succinimidyl terminated prepolymers are made by derivatizing the terminal hydroxyl groups of pentaerythritol ethoxylate or other polyols including hydroxyl terminated linear PEGs into carboxylate end groups by reacting them with anhydrides such as or glutaric, succinic or diglycolic anhydride, and then modifying the carboxylate groups into isocyanate groups via Curtius rearrangement or into the N-hydroxy succinimidyl ester groups via reaction with disuccinimidyl carbonate. Other hydroxyl terminated polymers that may be used to carry out reactions to form isocyanate or N-hydroxy succinimidyl terminated prepolymers, include without limitation, linear or multi-arm polyols derived from pentaerythritol or glycerol.

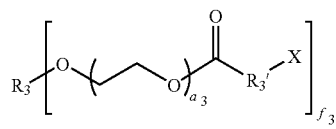
III

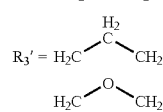

Where $3000 \geq a_3 \geq 3$; $6 \geq f_3 \geq 2$; $R_3$ may be a residue of a polyol, i.e., pentaerythritol, glycerols, polyalkylene glycol, and polyols having heteroatoms; and $R_3'$ may be —$CH_2CH_2$—, —$CH_2CH_2CH_2$— or —$CH_2OCH_2$—; and X is an electrophilic group including without limitation, isocyanate and N-hydroxysuccinimide ester.

Preferably, $a_3$ ranges from 3 to 500; and $f_3$ ranges from 2 to 4. The molecular weight of amine reactive moiety may range from about 250 to 10,000, preferably from about 250 to 4000, and more preferably from about 250 to 2000.

In a preferred but non-limiting embodiment, X is an isocyanate group as shown in the isocyanate terminated PEG prepolymer IIIa, having a molecular weight of ca 1350 and where $a_3$ ranges from 4 to 5.

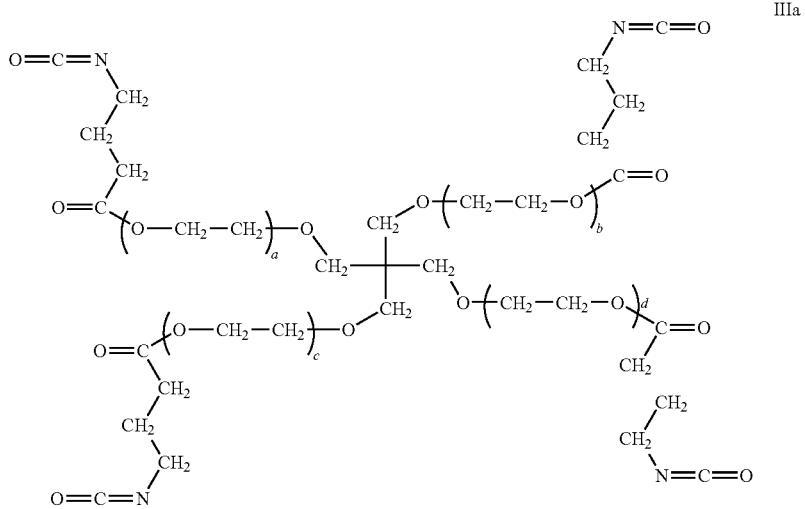
IIIa

Wherein $a + b + c + d \sim 15$

Alternatively, X may be an N-hydroxysuccinimide ester as shown in the N-hydroxysuccinimide ester terminated PEG prepolymer IIIb.

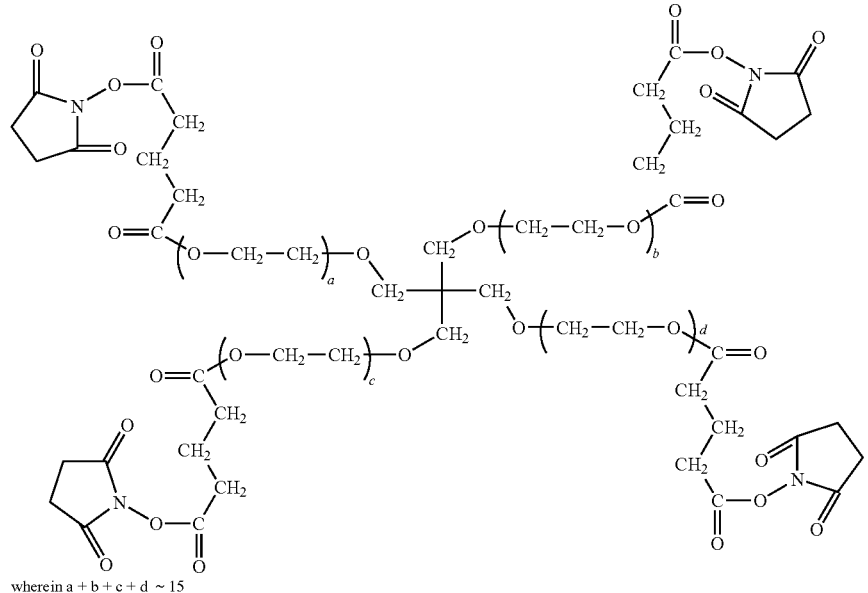

wherein a + b + c + d ~ 15

Alternatively, the amine reactive moiety having hydrolytically unstable ester linkages and electrophilic groups may be prepared from other hydroxyl terminated polymers such as linear or multi-arm biodegradable polyesters derived from monomers having hydrolytically unstable ester linkages, such as caprolactone, lactide, glycolide, dioxanone, trimethylene carbonate or their copolymers, to form isocyanate or N-hydroxy succinimde ester terminated prepolymers. Often it is desirable to have the hydrolysable ester located in the center of the amine reactive moiety with PEG chains surrounding it. In this way, reaction with a ketimine macromer having a hydrophobic backbone will result in a product that hydrolyzes to give water soluble breakdown products. Structures of this type are represented by IVa and IVb below.

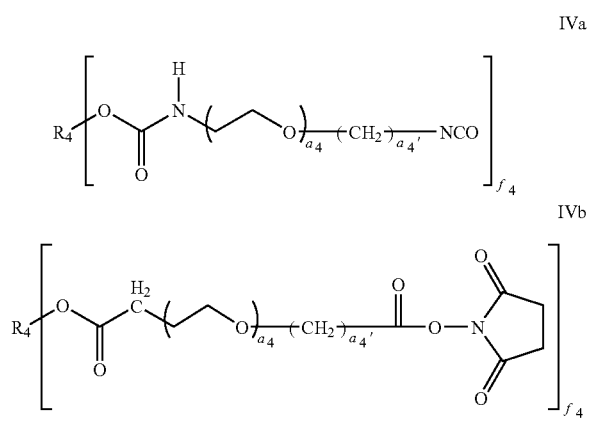

Wherein $10<a_4<50$, $1<a_4'<2$, $2<f_4<6$; $R_4$ is residue of a hydroxy terminated polyester synthesized by ring opening polymerization of various lactones and lactides, e.g. lactide, glycolide, caprolactone, trimethylene carbonate and p-dioxanone, glycerols and polyalkylene glycol. Alternatively, $R_4$ may be a polyester synthesized from condensation of alcohols and acids or esters.

Preferably, isocyanate or N-hydroxy succinimidyl terminated prepolymers IVa or IVb is made by reacting, in a 2:1 molar ratio, a diisocyanato PEG or di-N-hydroxy succinimidyl PEG with a hydroxyl terminated polymer such as linear or multi-arm biodegradable polyesters. To prepare these polyesters, cyclic monomers having hydrolytically unstable ester linkages, such as caprolactone, lactide, glycolide, dioxanone and trimethylene carbonate, are heated with an initiator, typically a small polyhydroxyl compound, in the presence of a suitable catalyst such as stannous octoate. The initiator's hydroxyloxygen attacks a ring carbonyl creating an ester bond as the ring's original ester linkage is cleaved to open the ring and form a new hydroxyl on the opposite end from the new ester bond. The new hydroxyl can similarly react with new monomer rings and the chain propagates. Alternatively, a suitable polyester can be prepared by reacting a polyacid such as adipic acid with an excess of PEG and a suitable catalyst (e.g. p-toluenesulfonic acid). creating a di-PEG adipate. These polyester syntheses are well known to those skilled in the art.

The Moisture Activated Latent Curing Adhesive or Sealant

The amine reactive moiety having hydrolytically unstable ester linkages and electrophilic groups and the ketimine or aldimine remain relatively stable when mixed together in a liquid mixture in the absence of moisture. By comparison, when the two component mixture is subjected to moisture, the polyethylene oxide)imine is "de-blocked" with water to reform the primary amine within about 30 seconds to 3 minutes, which then immediately reacts with the electrophilic groups of the amine reactive moiety, as shown in FIG. I.

In FIG. I, Z is a functional group formed from the reaction of the electrophilic group of the amine reactive moiety and the deblocked amine group of the ketimine or aldimine, including without limitation, a urea linkage when the electrophilic group is an isocyanate or an amide linkage when it is an N-hydroxy succinimide ester.

The moisture activated latent curing adhesive formed via the reaction of poly(ethylene oxide)imine Ia and isocyanate terminated PEG prepolymer IIIa has been designed to be biocompatible and biodegradable by utilizing predominantly PEG backbones in both Ia and IIIa, and incorporating hydrolytically unstable ester linkages in IIIa that will yield water soluble breakdown products, upon application and use in the human body.

As discussed above, a moisture activated latent curing adhesive may also be designed to be biocompatible and biodegradable even if the ketimine or aldimine has a hydrophobic backbone, by use of a biocompatible amine reactive moiety having hydrolytically unstable ester linkages located in the center of the amine reactive moiety with PEG chains surrounding it, for example IVa or IVb, whereby the degradation products of the moisture activated latent curing adhesive are water soluble.

This type of moisture-activated latent curing adhesive or sealant mixture offers tremendous benefits over the state of the art in terms of ease of use, delivery, handling, tissue adhesion and efficacy. Besides the moisture activation ability, key properties exhibited include effective sealing, adjustable cure speed, biocompatibility, and storage stability. By judicious selection of the polymer backbones and the location of the imine end-groups and the electrophiles, various other attributes, for example the rate of absorption and the degree of water-swellability, etc., may be tailored to suit one's needs.

While the following examples demonstrate certain embodiments of the invention, they are not to be interpreted as limiting the scope of the invention, but rather as contributing to a complete description of the invention.

EXAMPLE 1

Synthesis of Ketimine Ia, Isocyanate Macromer IIIa and their Gelation 24.42 g of a 4 armed, 4,000 molecular weight amine terminated PEG compound was weighed into a 250 mL round bottom flask. 31.94 g of methyl isopropyl ketone, MIPK (JTBaker) was added followed by the addition of 35.8 g of toluene (Aldrich Chemical), 0.30 g of glacial acetic acid (JT Baker) and a magnetic stir bar. The flask was equipped with a Dean Stark trap connected to a reflux condenser and nitrogen inlet for continuous nitrogen blanket and heated with mixing in an oil bath over a magnetic stir plate to 125° C. (oil bath temp). The water-toluene azeotrope began to distill over, separating into separate toluene and water layers in the Dean Stark trap shortly after the set temperature was reached. The reaction was allowed to continue in this way for 24 hours followed by removal of excess toluene, MIPK and acetic acid by distillation. The product was a brown viscous liquid that became a waxy solid upon cooling.

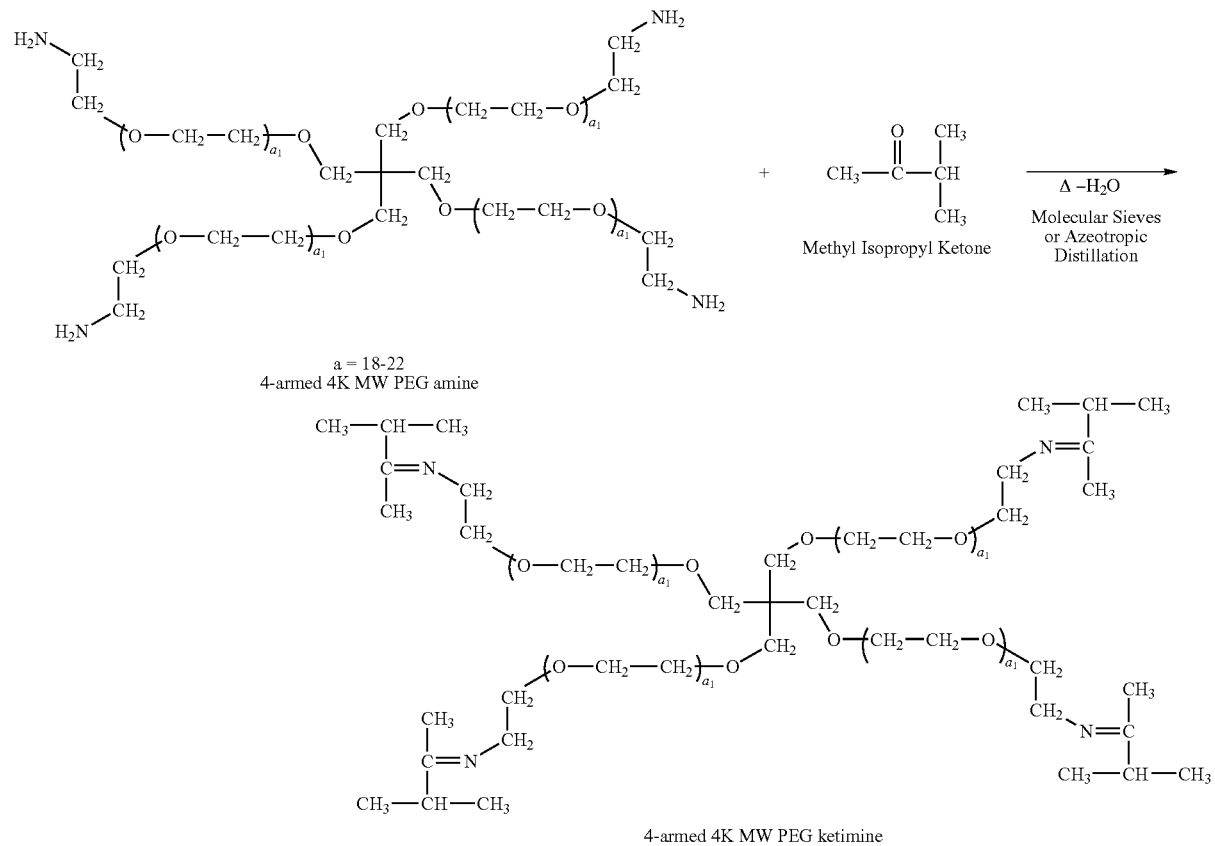

20 g of pentaerythritol ethoxylate (Aldrich chemical company) 100 mL of acetone (Aldrich chemical company, dried and distilled over calcium sulfate), 20 mL of triethylamine (Aldrich chemical company) was transferred into a dry round bottomed flask under nitrogen. To this was added with stirring, 10.9 g of glutaric anhydride (Aldrich chemical company) using a powder additional funnel. Reaction mixture was refluxed for 16 hours. Volatiles were evaporated in vaccuo. To residue was added 100 mL of water and extracted 1×75 mL of dichloromethane (Aldrich chemical company). The organic extract was dried over anhydrous sodium sulfate, filtered and volatiles were evaporated first on rotovap and then under high vacuum at 115° C. for 1 hour to obtain 15.6 g of multi-arm acid. 10.0 g of multi-arm acid was transferred into a 250 mL flask and 50 mL of anhydrous dichloromethane was cannulated into the flask while stirring. To the homogeneous mixture was added 6.0 g of thionyl chloride (Aldrich chemical company) via dry syringe and reaction mixture was refluxed for 1 hour. An FTIR recorded at this stage showed no COOH and presence of COCl. Solvent was evaporated under high vacuum and 30 mL of dry toluene was added to the reaction flask followed by addition of 6.0 g of azidotrimethylsilane (Aldrich chemical company). Temperature of the reaction mixture was gradually increased and formation of bubbles signified commencement of Curtius rearrangement. After formation of bubbles subsided, reaction flask was held at 80° C. for 10 min to ensure complete conversion of acyl azide to isocyanate groups. Solvent was first evaporated under high vacuum at room temperature and then for 5 min at 70° C. to obtain 9.7 g light brown colored liquid.

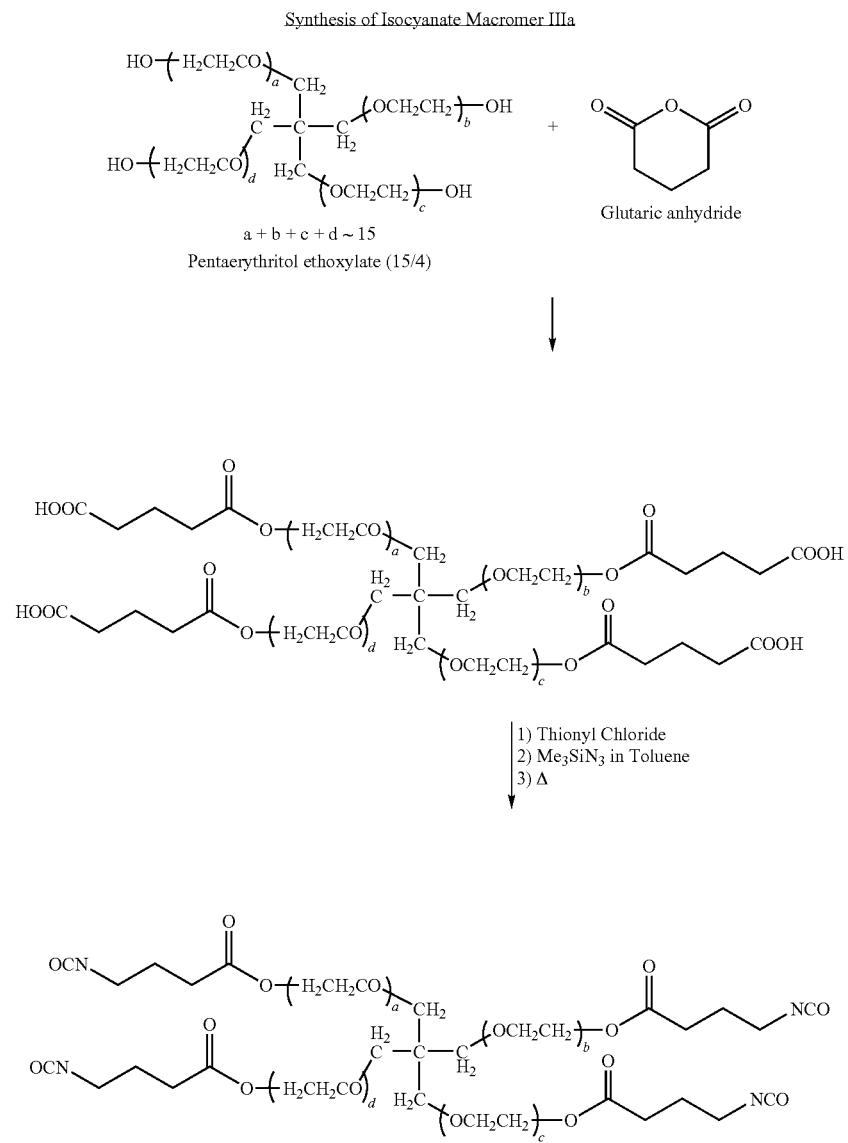

A mixture comprising ketimine Ia and the tetrafunctional isocyanate macromer IIIa was allowed to react via the scheme shown in FIG. II.

An Ex-vivo Arterial Anastomoses Model:

In this model, anastomosis were performed on porcine carotid arteries. This was followed by pressurizing the sutured artery to slowly increase the fluid pressure inside the sutured artery, until failure was noted by the leaking of fluid from the suture line. The pressure at failure was noted as the baseline and typically ranged between 40-60 mm Hg.

The ketimine Ia, 70% in N-methylpyrolidone, and the isocyanate macromer IIIa were mixed to form a viscous stable liquid, which was then applied to the suture line and allowed to cure. The fluid pressure was increased again and the pressure at failure was noted. The ketimine based sealant cured after being applied to the wet vessels in 2-3 minutes and pressures at failure ranged from 251 to 537 mm Hg in three separate runs.

EXAMPLE 2

Synthesis of a Triketimine and an Amine Reactive Moiety Having an Electrophilic Group and Absorbable Ester Linkages

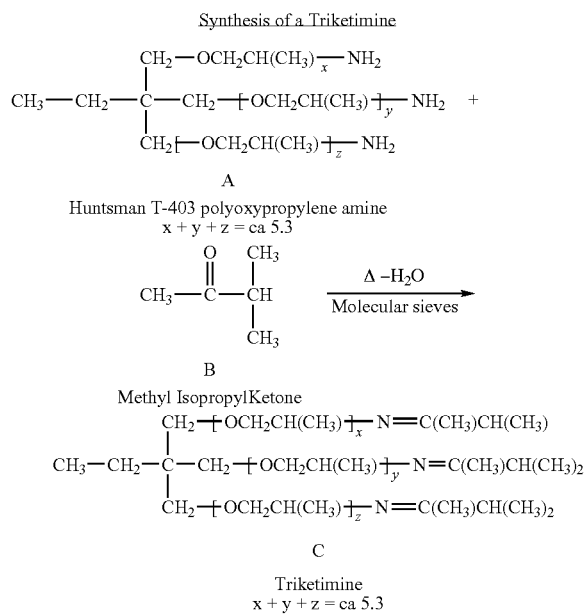

40 g of amine terminated polypropylene glycol (Huntsman T-403) was weighed into a 250 mL round bottom flask. 20 g of 4 A° molecular sieves were added to the flask followed by 24.48 g of methyl isopropyl ketone (JT Baker). The flask was equipped with a magnetic stir bar and heated to an internal temperature of 70° C. for 3 days. The product was isolated by centrifugation followed by filtration through a 0.45 micron syringe filter and was a clear, slightly yellow liquid. Using the tri-amine precursor A allowed for higher crosslink density materials and higher strength. The reaction is as depicted above.

An amine reactive moiety having electrophilic groups and absorbable ester linkages was prepared according to FIG. III. Specifically, 5.32 g of an isocyanate terminated 2000 molecular weight PEG powder was weighed, in a glove box under dry nitrogen, into a 50 mL round bottom flask. 0.41 g of a dried 600 molecular weight liquid caprolactone/glycolide diol was added followed by addition of 2.36 g of dry N-methylpyrolidone. The reaction mixture was heated in an oil bath over a magnetic stir plate, under dry nitrogen, to 65° C. at which point a single clear phase resulted. 0.08 g of a 1% solution of Bicat H (Shephard chemical) bismuth catalyst in toluene was added. The reaction mixture was heated to 80° C. and kept at that temperature for 4.5 hours. The product was a clear slightly brown liquid that became a waxy solid upon cooling. The wt % free isocyanate as determined by titration was 1.65%

Biocompatibility of the Two-component Cured System

The triketimine was mixed with the degradable PEG/polyester diisocyanate in a 1:1 equivalent ratio of NCO:Ketimine prior to application to a tissue and then implanted in rats for a subcutaneous tissue reaction and absorption study.

An exploratory 7, 14, 28-day subcutaneous tissue reaction and absorption study of the above system in rats was carried out. At days 7, 14 and 28 post implantation, the tissue reaction to the saline control was characterized by minimal sub-acute inflammation, minimal to mild capillary proliferation and minimal fibrosis. At day 7, the sealant resulted in mild to moderate chronic inflammation, minimal to mild capillary proliferation and the presence of a generally mild amount of the free sealant material. At day 14, the sealant material had phagocytized by the histiocytes and was interpreted to be absorbed in 40% of the implant sites. At day 28, the sealant material was interpreted to be absorbed at all the implant sites. At days 14 and 28, a decrease in severity of the inflammatory reaction was observed. At day 28, mild to moderate histiocytosis was observed in the inguinal_lymph node of all the animals. These histiocytes were interpreted to have phagocytized the sealant material. No systemic effects were observed in the kidneys, liver and spleen, there appears to be a low or no incidence for acute systemic toxicity. The above was considered a favorable response of the animal to the sealant formulation.

What is claimed is:

1. A isocyanate terminated PEG prepolymer represented by formula IIIa:

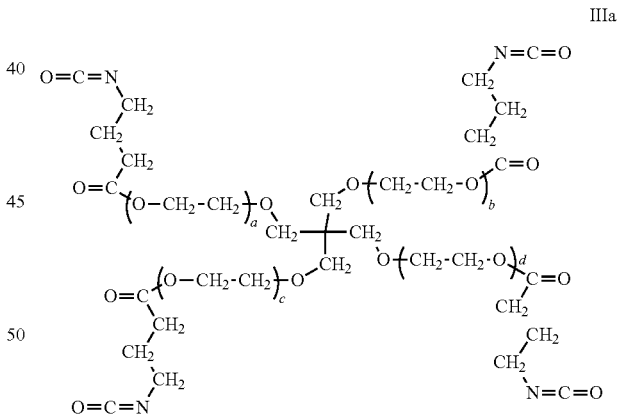

wherein a, b, c and d each range from 3 to 500.

* * * * *